United States Patent
Johansson-Rudén et al.

(10) Patent No.: US 6,428,561 B1
(45) Date of Patent: Aug. 6, 2002

(54) BIOCOMPATIBLE GLUE

(75) Inventors: Gunilla Johansson-Rudén, Askim; Bengt Söderström, Göteborg, both of (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 08/875,129

(22) PCT Filed: May 30, 1997

(86) PCT No.: PCT/SE97/00945
§ 371 (c)(1),
(2), (4) Date: Jul. 17, 1997

(87) PCT Pub. No.: WO97/46632
PCT Pub. Date: Dec. 11, 1997

(30) Foreign Application Priority Data

Jun. 5, 1996 (SE) .............................. 9602226

(51) Int. Cl.⁷ .............................. A61B 17/08; A61D 1/00
(52) U.S. Cl. .................... 606/214; 623/925; 623/23.75; 523/105; 424/423
(58) Field of Search ........................ 623/11, 925, 23.75, 623/23.76, 11.11, 15.12; 424/423; 523/105, 118; 602/56; 606/214

(56) References Cited

U.S. PATENT DOCUMENTS

| | | | | |
|---|---|---|---|---|
| 3,873,333 A | | 3/1975 | Hijiya et al. | |
| 3,903,889 A | * | 9/1975 | Torr | 128/287 |
| 4,055,669 A | * | 10/1977 | Kelly et al. | 426/93 |
| 4,530,942 A | * | 7/1985 | Dhabhar et al. | 523/118 |
| 4,738,257 A | * | 4/1988 | Meyer et al. | 602/56 |
| 4,952,618 A | * | 8/1990 | Olsen | 602/56 |
| 5,192,802 A | * | 3/1993 | Rencher | 523/118 |
| 5,503,638 A | | 4/1996 | Cooper et al. | |
| 5,622,168 A | * | 4/1997 | Keusch et al. | 607/149 |
| 5,631,011 A | * | 5/1997 | Wadstrom | 424/400 |
| 5,690,675 A | * | 11/1997 | Sawyer et al. | 606/214 |
| 5,863,322 A | * | 1/1999 | Van De Heisteeg et al. | 106/617 |

FOREIGN PATENT DOCUMENTS

| | | |
|---|---|---|
| EP | 0667119 | 8/1995 |
| JP | 61250080 | * 11/1986 |
| SU | 1438802 | 11/1988 |
| WO | WO 9222606 | 12/1992 |
| WO | WO 9428937 | 12/1994 |

* cited by examiner

Primary Examiner—Paul B. Prebilic
(74) Attorney, Agent, or Firm—White & Case LLP

(57) ABSTRACT

Use of one or more saccharides, for example one or more non-toxic mono-, di-, tri-, oligo- or polysaccharides, in the manufacture of a biocompatible glue for adhering a first structure to a surface of a second structure. The biocompatible glue can be adapted to act as a temporary glue. In this case the glue may be used to enable a medical structure to be transferred from a medical instrument onto the surface of a structure of a human or animal body, for example as in the transfer of a buffer material from the fork of a surgical stapler to a diseased lung after one or more rows of staples have been fired through the buffer material into the lung during lung volume reduction surgery for treating emphysema. The biocompatible glue can also to advantage be used to adhere or secure medical structures to a structure of a human or animal body direct, such as in the case of a patch being applied to the skin of a mammal.

11 Claims, No Drawings

BIOCOMPATIBLE GLUE

TECHNICAL FIELD OF THE INVENTION

The present invention relates to a new use of a known material in the manufacture of a biocompatible glue for adhering a first structure to a surface of a second structure, the invention having particular, although not exclusive, application in surgery or other medical procedures such as lung volume reduction for treatment of emphysema or treating a bodily organ or tissue. It also relates to a medical device comprising a patch of polymeric material provided with a coating of such a glue.

BACKGROUND OF THE INVENTION

Emphysema is a condition of the lung characterised by the lung capacity tending to decrease. After a patient has contracted the disease typically only 15 to 20 per cent of the normal lung capacity can remain. To improve the lung capacity around about 30 per cent of the lung volume is cut off by trimming away part of the lung in a procedure known as lung volume reduction surgery to help the healthy tissue to expand and thus improve lung capacity. The usual way of achieving this is by using a linear surgical stapler to place two rows of closely spaced staples along the line of the desired cut and then cutting along the line of staples. This is generally done between the rows although it may also be done on the diseased side of the lung close to one of the rows. This process may be performed several times until the most affected part of the lung has been completely cut away.

When lung volume reduction surgery or other lung surgical procedures are performed a common complication is persistent air leaks which result in a significant and prolonged air loss from the lung. This has been reported to be mainly through the staple holes which can expand or tear when the lung is re-inflated.

The incidence of air leaks, however, may be reduced through the application of a strip of material to the stapler and inserting the staples through the strip. For example, in EP-A-0667119 (Bio-Vascular, Inc.) there is made known an article of manufacture comprising a strip of animal tissue material comprising bovine pericardium which is temporarily fastened to a buttress member by means of a basting filament to define a tubular configuration which is able to slide over one of the jaws or forks of a surgical staple gun. The strip of animal tissue material is so arranged on the fork that the staples are inserted through the strip. The diseased tissue is then cut away. The diseased tissue thus remains temporarily attached to the healthy tissue at this stage as the buttress member is still attached to the strip. Removal of the basting filament is required to free the buttress from the strip and thus the diseased tissue from the healthy tissue.

There are several disadvantages to the means proposed in EP-A-0667119 for positioning the strip of animal material on the fork of the staple gun such that staples can be fired therethrough into the diseased lung.

First, cutting away of the diseased tissue does not effect its removal until the buttress member has also been severed from the strip. Second, the buttress member makes it difficult to cut the tissue especially in endoscopic techniques as it tends to get in the way. Third, the strip of animal tissue is only loosely held on the surgical stapler by the buttress member and could easily fall off. This is again problematic particularly if endoscopic techniques are being used.

DISCLOSURE OF THE INVENTION

The present invention proposes to provide means for adhering or securing a first structure to a surface of a second structure which may be used in the medical field.

Thus, according to the present invention there is provided the use of one or more saccharides in the manufacture of a biocompatible glue for adhering a first structure to a surface of a second structure. For example, one or more non-toxic mono-, di-, tri-, oligo-or polysaccharides may be used in the manufacture of the biocompatible glue.

In an embodiment of the invention the biocompatible glue is adapted for releasably adhering the first structure to the surface of the second structure. This has particular application where the first structure is a medical structure for disposal on a surface of a human or animal body structure and the second structure is a medical instrument The biocompatible glue then enables the medical structure to be transferred from the medical instrument onto the surface of the body structure. For example, the body structure may be an internal structure of the human or animal body and the medical instrument an invasive surgical instrument for an invasive surgical procedure in which the medical structure is to be transferred from the surgical instrument to the surface of the internal body structure. Lung volume reduction surgery involves such a surgical procedure. In this case, the medical structure may serve as a buffer material to reinforce one or more lines of staples fired into a diseased lung to prevent air leaks following surgery. There would be no need for the glue to assist in the adhesion of the buffer material to the bodily organ once the material has been removed from the surgical instrument The glue simply needs to act as a temporary glue during the surgical procedure.

Other surgical procedures in which the invention may be used include intestinal anastomosis and vascular surgery. In vascular surgery, the buffer material would serve to prevent the loss of blood not of air as in lung volume reduction surgery.

The buffer material may be a strip of animal tissue material comprising bovine pericardium, as disclosed in EP-A-0667119 (Bio-Vascular, Inc.). However, this has the disadvantage that the polymer that makes up bovine pericardium is non-resorbable and non-degradable in the patient over the time period in which it is present, especially as it would tend to calcify. Other non-degradable materials that may be used include TEFLON, i.e. poly(tetrafluoroethylene), and DACRON, a polyester material of poly(ethylene terephthalate). Ideally, though, the material is a bio-resorbable material. Suitable bio-resorbable materials include polymers such as poly(glycolic acid) (PGA), poly (lactic acids) (PLA), poly($\epsilon$-caprolactone) (PCL), poly($\beta$-malic acid) (PMLA) and poly($\rho$-dioxanone) (PDS). Poly($\beta$-hydroxybutyric acid), generally referred to as poly(3-hydroxybutyrate) (PHB), is particularly suitable, on account of it being degradable, biocompatible and resorbable. It may further be formed into a non-woven patch.

In an alternative embodiment of the invention the first structure is a medical instrument and the second structure an organic tissue structure such as the skin or hair of mammals. The biocompatible glue may then be used in any application where a medical instrument needs to be stuck to the skin or hair of mammals. For example, the glue may be used for sticking electrodes or a compress to the skin or hair.

In another embodiment of the invention the second structure is a human or animal body structure and the first structure is a medical structure. The medical structure may be applied direct to the body structure, for example a medical patch applied to the skin of a mammal. In such a case, there is no need to use a medical instrument to facilitate its application.

The composition of the biocompatible glue may vary according to the particular application for which it is to be used. Depending on the viscosity of the glue that is required, up to 90% by weight of saccharides might be used in solution. However, a glue containing from 60 to 90% by weight of saccharides is preferred. A glue containing from 80 to 85% by weight of saccharides, especially an amount in the vicinity of 85% by weight, is particularly preferred.

Any solvent may be used in the glue, but water is an ideal solvent to ensure bio-compatibility.

The viscosity of the glue also depends on the type of saccharide that is used. Furthermore, polysaccharides are not all easily resorbed by the human body and some are toxic. For this reason, sugars, i.e. mono- and disaccharides, are ideal because they are non-toxic and quickly resorbable. Commonly occurring mono- and disaccharides such as fructose, glucose (dextrose) and sucrose may be used.

The glue may be applied in the form of a solution and then dried. The material may then be moistened immediately prior to use. When a biodegradable material such as poly (3-hydroxybutyrate) is used, however, there is the danger that the material may hydrolyse during manufacture or storage. The glue may also be used as a separate supply of dry powder, again moistened immediately prior to use. However, more control can be had over the composition of the glue, ensuring the optimal ideal stickiness is achieved, if it is applied in a viscous state and used immediately. This also obviates the addition of water at the time of use.

The glue may contain a single type of saccharide, i.e. be composed of one saccharide only in solution. This is perfectly acceptable when the glue is applied in the form of a solution and then dried. A mixture of two or more different saccharides is preferred, however, to obviate possible problems with crystallisation.

Water loss from the glue during storage may be minimised by adding a hygroscopic material. The hygroscopic material may include 0.5 to 30% by weight of glycerol. 1 to 10% by weight of glycerol is preferred with around about 10% being most preferred. Alternatively, the hygroscopic material may include 1 to 30% by weight of polyethylene glycol (PEG) having a molecular weight of less than 50000. This has the further advantage that it may act as a lubricant.

According to the invention there is further provided a biocompatible glue comprising one or more saccharides for adhering a first structure to a surface of a second structure.

According to the invention there is yet further provided a method of adhering a first structure to a surface of a second structure comprising the step of applying a coating of a biocompatible glue comprising one or more saccharides to one or other of the first or second structures.

According to the invention there is also provided a method of treatment of a human or animal body by surgery including the steps of releasably securing a medical structure to a surgical instrument and then transferring the medical structure from the surgical instrument to a surface of a structure of the human or animal body characterised in that the medical structure is releasably secured to the surgical instrument with a biocompatible glue comprising one or more saccharides.

According to the invention there is additionally provided a medical device comprising a patch of polymeric material and a coating of a biocompatible glue comprising one or more saccharides for adhering the patch to a surface of a structure of a human or animal body. Suitable polymeric materials include non-degradable materials such as bovine pericardium, TEFLON, i.e. poly(tetrafluoroethylene), and DACRON, a polyester material of poly(ethylene terephthalate). Ideally, though, the material is a bio-resorbable material. Suitable bio-resorbable materials include polymers such as poly(glycolic acid) (PGA), poly (lactic acids) (PLA), poly($\epsilon$-caprolactone) (PCL), poly($\beta$-malic acid) (PMLA) and poly($\rho$-dioxanone) (PDS). We have found that poly($\beta$-hydroxybutyric acid), generally referred to as poly(3-hydroxybutyrate) (PHB), is particularly suitable, on account of it being degradable, biocompatible and resorbable. It may also be used as a non-woven patch.

DETAILED DESCRIPTION OF EMBODIMENTS OF THE INVENTION

Embodiments of the invention will now be described by way of example. These illustrate the use of one or more saccharides in the manufacture of a biocompatible glue for sticking a medical instrument or a bodily organ or tissue to another material. The glue is either prepared as (1) a wet glue and applied to
      (a) a linear cutter surgical stapler, and
      (b) human skin, or
   (2) a dry glue, moistened immediately prior to use.

(1) Wet Glue 30 g of water was heated in a beaker covered by plastic foil to 70° C. 40 g of sucrose, 30 g of fructose and 30 g of glucose (dextrose) were added to the water dissolved by agitation at 70° C. for approximately 30 minutes. The plastic foil was removed and the water evaporated for approximately 2 hours until the saccharides formed around about 85% by weight of the solution. The solution was then placed in a glass syringe (1 ml) and cooled down to ambient temperature ready for use.

(a) Linear Cutter Surgical Stapler

A small amount (less than 1 ml and preferably 0.05–0.1 ml) of the solution was spread out on each of two strips (1 cm by 10 cm) of a non-woven patch made of poly(3-hydroxybutyrate) (PHB). The strips were then put on the forks of a linear cutter surgical stapler, PROXIMATE® model TLC-75 as supplied by Ethicon, Inc., of Somerville, N.J., USA. The strips stuck easily to the forks and after the instrument was fired the strips were easily removed from the forks.

(b) Skin

A small amount (less than 1 ml) of the solution was spread out on a piece (5 cm by 5 cm) of a non-woven patch made of PHB. The patch was then put on the skin and the patch was easily stuck to the skin. Even after 10 hours the patch was still adhering to the skin yet easily able to be removed.

(2) Dry Glue 10 g of water was heated in a beaker covered with a plastic foil to 70° C. 30 g of sucrose was added to the water and the sucrose was dissolved by agitation at 70° C. for half an hour. The plastic foil was removed and 1 ml of the solution spread out on a strip (1 cm by 10 cm) of a non-woven patch made of poly(3-hydroxybutyrate) (PHB). The strip was then put in a vacuum oven at 50° C. for 5 hours in order to evaporate the water. The strip was then wetted with a moistened sponge and put on a fork of a linear cutter surgical stapler. The strip stuck easily to the fork and was also easy to remove.

What is claimed is:

1. A biocompatible glue comprising one or more mono-, di-, tri- or oligosaccharides in solution, which is adapted for releasably adhering a first structure to a surface of a second structure, wherein the saccharides comprise at least 60% by weight of the total weight of the glue and wherein the solution includes 0.5 to 30% by weight, based on the total weight of the glue, of glycerol.

2. A biocompatible glue comprising one or more mono-, di-, tri- or oligosaccharides in solution, which is adapted for releasably adhering a first structure to a surface of a second structure, wherein the saccharides comprise at least 60% by weight of the total weight of the glue and wherein the solution includes 1 to 30% by weight, based on the total weight of the glue, of polyethylene glycol having a molecular weight of less than 50,000.

3. A biocompatible glue comprising a mixture of two or more different mono-, di-, tri- or oligosaccharides, which is adapted for releasably adhering a first structure to a surface of a second structure, wherein the saccharides comprise at least 60% by weight of the total weight of the glue and wherein the saccharides comprise sugars.

4. A biocompatible glue comprising one or more mono-, di-, tri- or oligosaccharides in solution, which is adapted for releasably adhering a first structure to a surface of a second structure, wherein the saccharides comprise approximately 85% by weight of the total weight of the glue and wherein the solution includes 0.5 to 10% by weight, based on the total weight of the glue, of glycerol.

5. A biocompatible glue comprising one or more mono, di-, tri- or oligosaccharides in solution, which is adapted for releasably adhering a first structure to a surface of a second structure, wherein the saccharides comprise approximately 85% by weight of the total weight of the glue and wherein the solution includes polyethylene glycol having a molecular weight of 50,000.

6. A biocompatible glue as claimed in claim 4, wherein water is used as a solvent for the saccharides to form the solution.

7. A biocompatible glue as claimed in claim 5, wherein water is used as a solvent for the saccharides to form the solution.

8. A biocompatible glue comprising one or more mono-, di-, tri- or oligosaccharides in solution, which is adapted for releasably adhering a first structure to a surface of a second structure, wherein the saccharides comprise approximately 85% by weight of the total weight of the glue and wherein water is used as a solvent for the saccharides to form the solution.

9. A biocompatible glue comprising one or more mono-, di-, tri- or oligosaccharides in solution, which is adapted for releasably adhering a first structure to a surface of a second structure, wherein the saccharides comprise approximately 85% by weight of the total weight of the glue and wherein the saccharides comprise sugars.

10. A biocompatible glue as claimed in claim 9, which glue comprises a mixture of two or more different saccharides.

11. A method of treatment of a human or animal body by surgery including the steps of releasably securing a medical structure to a surgical instrument and then transferring the medical structure from the surgical instrument to a surface of a structure of the human or animal body wherein the medical structure is releasably secured to the surgical instrument with a biocompatible glue according to any of claims 1, 2, 4–8, 9, 3 or 10.

* * * * *